United States Patent [19]

Pecina

[11] 4,150,071
[45] Apr. 17, 1979

[54] NEBULIZER

[75] Inventor: Richard W. Pecina, Waukegan, Ill.

[73] Assignee: Respiratory Care, Inc., Arlington Heights, Ill.

[21] Appl. No.: 828,043

[22] Filed: Aug. 26, 1977

[51] Int. Cl.² .................. B01F 3/04; A61M 15/00
[52] U.S. Cl. .................. 261/78 A; 128/194;
239/338; 239/370; 261/DIG. 65
[58] Field of Search .......... 261/1, 78 A, 81, DIG. 48,
261/DIG. 65; 128/193, 194, DIG. 2; 239/120,
338, 370; 55/257 R

[56] References Cited

U.S. PATENT DOCUMENTS

| 816,656 | 4/1906 | Gurnee | 239/338 |
| 923,822 | 6/1909 | Dorment | 239/338 X |
| 1,839,193 | 1/1932 | Blanchard | 239/338 X |
| 2,951,644 | 9/1960 | Mahon et al. | 239/338 X |
| 3,004,718 | 10/1961 | Gorman | 239/338 X |
| 3,104,062 | 9/1963 | Mahon | 128/194 X |
| 3,825,000 | 7/1974 | Huggins | 261/78 A X |
| 3,857,909 | 12/1974 | Huggins | 261/78 A X |
| 3,915,386 | 10/1975 | Vora | 128/194 X |
| 3,929,128 | 12/1975 | Pekkarinen | 128/194 |
| 3,944,635 | 3/1976 | Siegenthaler | 261/78 A X |

FOREIGN PATENT DOCUMENTS 9827 of 1905 United Kingdom ............... 239/338

Primary Examiner—Richard L. Chiesa
Attorney, Agent, or Firm—Eric P. Schellin

[57] ABSTRACT

The invention relates to a nebulizer of simple three-piece construction, adapted by its design to be injection molded for delivering to a patient, entrained in a stream of oxygen or other gas flowing at a modest rate (such as 6 to 8 liters a minute) a quantity of liquid supplied from a unit-dose hermetically sealed vial. The entire nebulizer with unit-dose vial attached, fits the hand of the patient, and its small size and the use of a unit-dose vial simplifies self-administration by an out-patient. Also disclosed is an adapter for connecting the nebulizer to a mouthpiece, with means permitting the patient to control the concentration of the mist delivered to the lungs.

14 Claims, 17 Drawing Figures

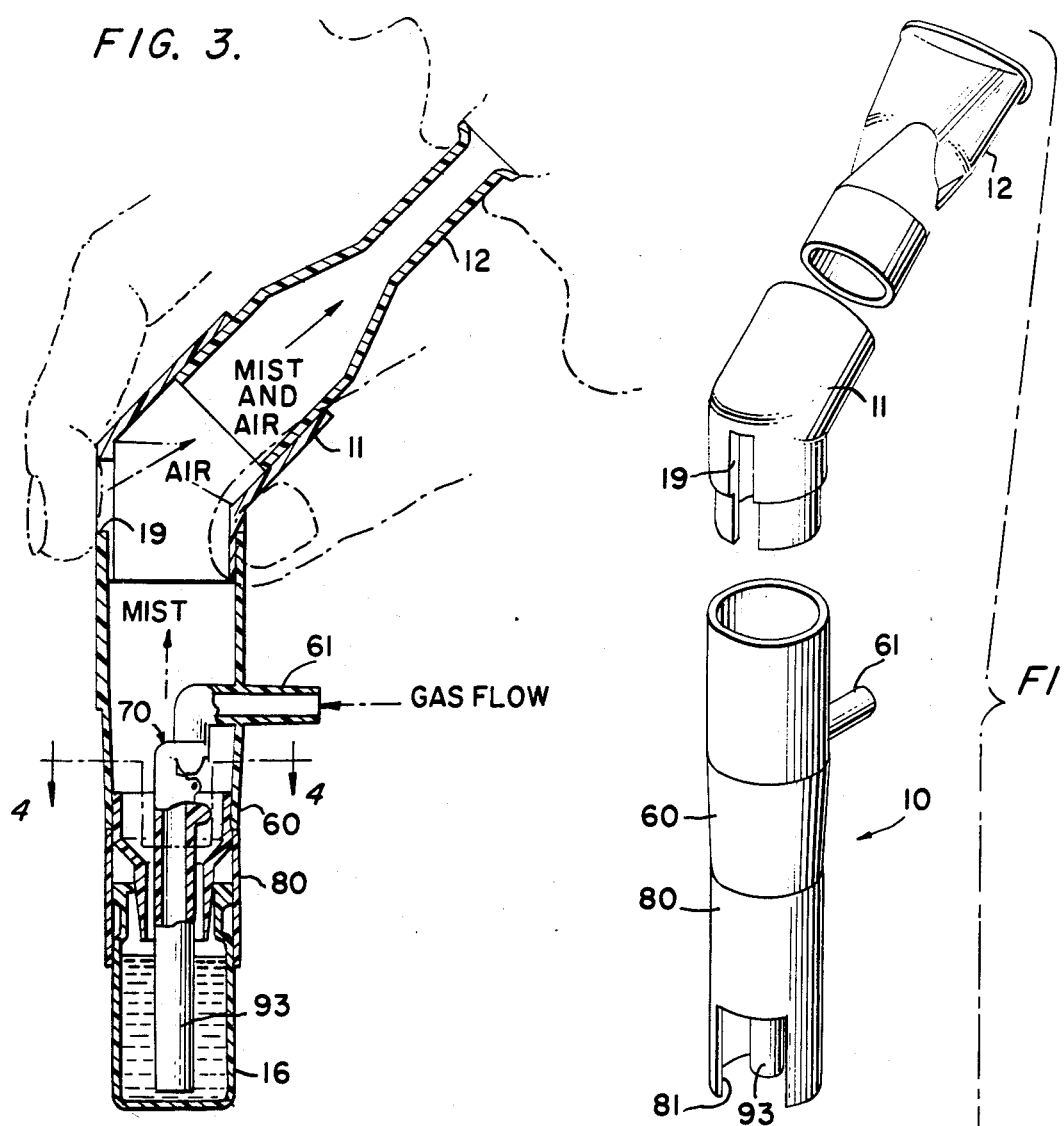

FIG. 7A.
FIG. 7B.
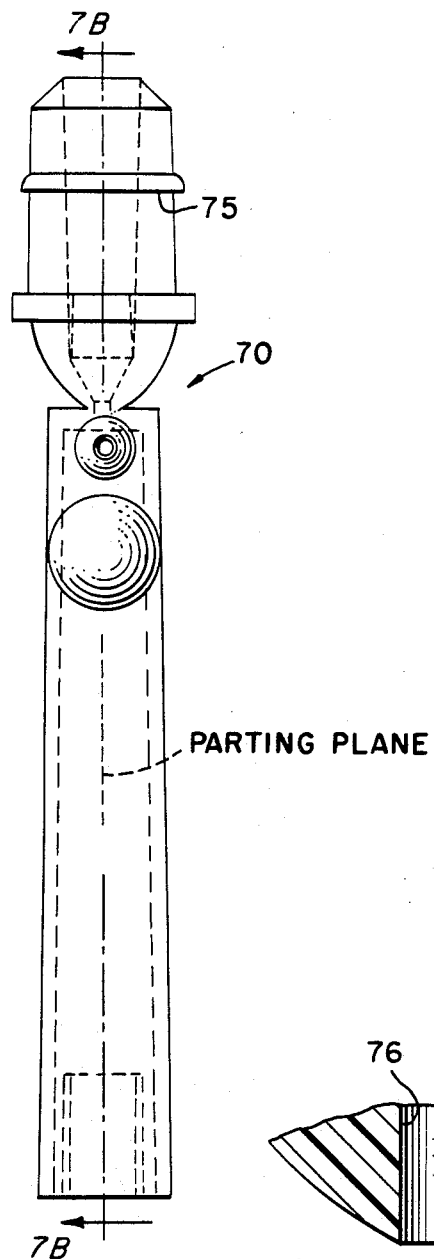
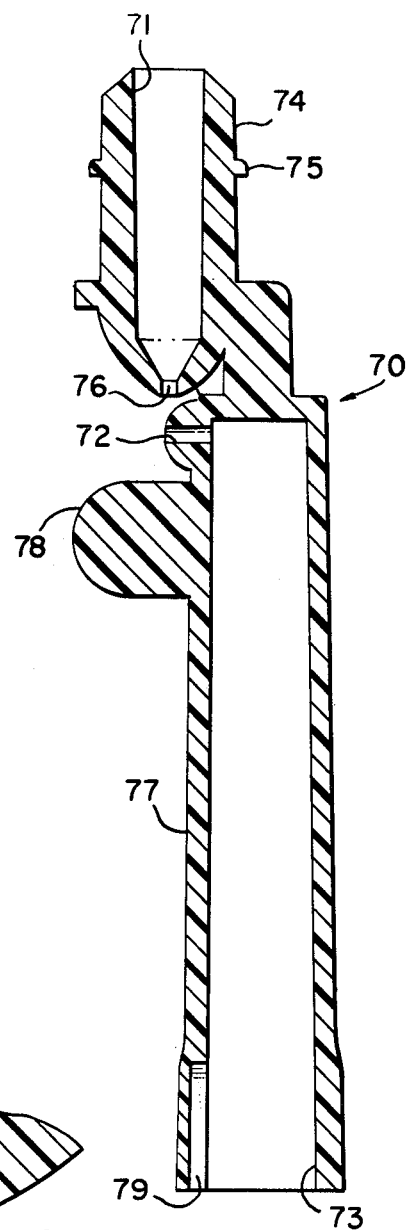
FIG. 7C.
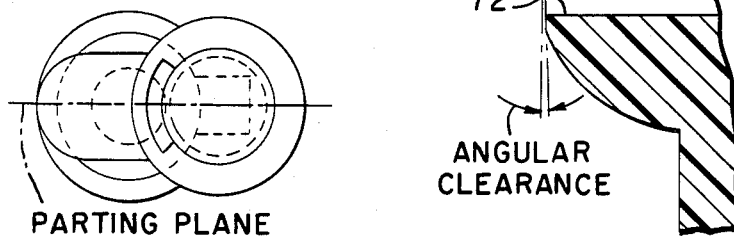
FIG. 7D.

4,150,071

NEBULIZER

BRIEF SUMMARY OF INVENTION

In many kinds of lung disease it is necessary to deliver to the alveoli a small amount of medication or moisture. For example, in cystic fibrosis, asthma, and chronic obstructive pulmonary disease, thick phlegm in the lungs must be expelled, and this is assisted by thinning the phlegm with medication or moisture, delivered as a mist.

One form of therapy for doing this is by use of intermittent positive pressure breathing apparatus, which generally requires hospitalization and skilled attention. Where the condition is not extremely severe, it is possible to use nebulizers, which entrain the medication or moisture in a stream of air or oxygen to produce a mist which is breathed in by the patient under ambient pressure conditions. This is especially desirable for elderly or child patients, who often cannot tolerate pressure breathing.

The instant invention relates to a simple nebulizer of the ambient pressure type, wherein the medication or moisture is entrained in a modest current of air, supplied by a compressor, or oxygen, supplied by an oxygen cylinder.

The nebulizer is of relatively small size, so that it can be held in the palm of the patient's hand, with the unit-dose vial of medicine or moisture enclosed. Thus the patient can hold the device much as a smoker holds a pipe, and can readily raise the mouthpiece to his lips. This renders the device ideal for out-patient home use. The flow of gas needed to entrain the medication or moisture, in a particular embodiment on which the instant drawings are based, is a modest 6 to 8 liters per minute. In said embodiment, the medication or moisture in the small vial, holding 3–5cc of pure or medicated water, will be entrained in the flowing gas at a reasonably uniform rate for 10 to 15 minutes before being exhausted, and this length of time is convenient for treatment.

The 6 to 8 liters per minute of oxygen or air can be readily supplied from a conventional medical-oxygen cylinder, holding 250 cubic feet (over 9000 liters). Thus such a standard cylinder can be used for many treatments, in view of the small demand of oxygen.

The use of unit-dosage vial, the small size of the device, and the modest demand on oxygen, is advantageous for self-treatment by an out-patient.

In order to reduce costs, the basic nebulizer is built up of three injection molded parts.

An adapter connects the nebulizer to the patient's mouth for inhalation. The adapter includes a by-pass hold which can readily and selectively be blocked by the patient's finger to control mist concentration.

BRIEF DESCRIPTION OF SEVERAL VIEWS OF DRAWINGS

FIG. 3 is a side view, partly in cross-section, taken along the plane 3—3 of the nebulizer of FIG. 2, with the unit-dose vial inserted, and showing how the device is held by the patient.

FIG. 4 is a cross-section, taken along the plane 4—4 of FIG. 3.

FIG. 5 is a partially exploded view of the nebulizer of the preceding figures.

FIGS. 7A, 7B and 7C are respectively a front view, a cross-sectional view taken along the plane 7B—7B of FIG. 7A and a bottom view of the venturi of the nebulizer, while FIG. 7D is an enlarged cross-sectional view of the critical portion of the venturi.

FIGS. 8A and 8B are respectively side and front views taken along the planes 8A—8A and 8B—8B of FIG. 8C, while

DETAILED DESCRIPTION

Figure 1:
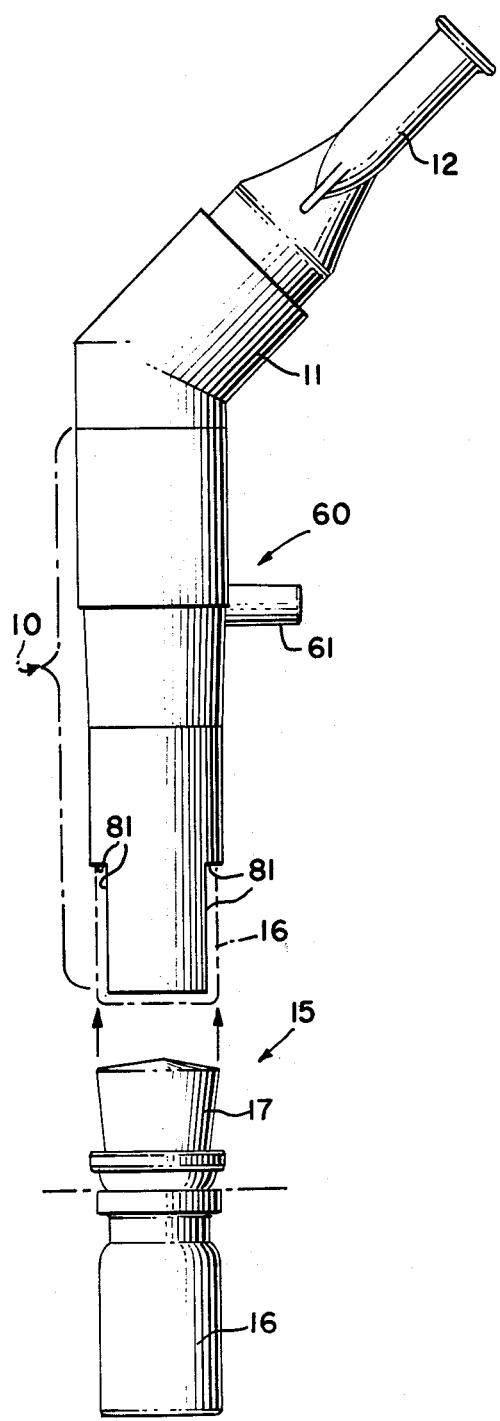
FIG. 1 is a side view of the noval nebulizer, with a unit-dose hermetically sealed capped vial situated below.
Figure 2:
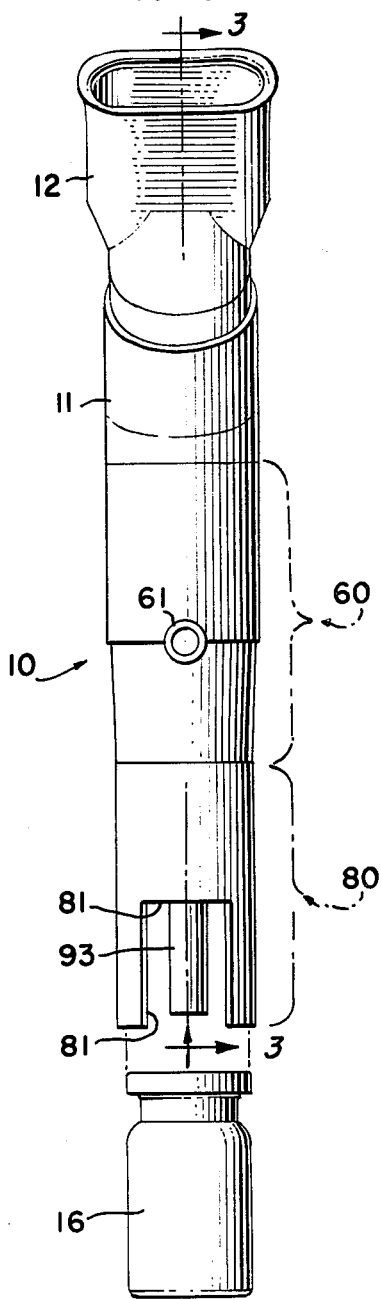
FIG. 2 is a front view, corresponding to FIG. 1 of the nebulizer and the unit-dose vial. The vial is shown with cap torn off, situated below the nebulizer, ready for insertion.

As shown in FIGS. 1 and 2, the nebulizer 10 comprises an upper body 60 and a lower body and vial holder 80.

An inlet tube 61 is an integral part of the upper body 60 and is adapted to be connected to a source of gas, such as air or medical oxygen, which flows into the inlet tube 61 at a moderate rate.

The flowing gas passes through the nozzle of a venturi unit, not shown in FIGS. 1 or 2, which sucks up liquid contained in a body 16 of a unit-dose vial 15, and entrains some of that liquid in the flowing gas as a mist.

The mist thereby produced flows up through the upper body 60 into an elbow 11 to a mouthpiece 12, which the patient puts into his mouth to inhale the mist.

The unit-dose vial 15 may be a hermetically sealed plastic blow-molded container, which contains the liquid (which may be pure sterile water or a medicine). It is contemplated that the container is filled while still within the blow mold and before a cap 17 is formed and sealed. Since the blowing of a container from the plastic parison occurs at temperatures far above the boiling point of water, the inside of the unit-dose vial 15 and its sterile filling will continue to remain sterile after discharge from the blow-molding and filling machine.

For use, the cap 17 of the unit-dose vial 15 is removed from the body 16 by breaking it away. To assist in readily removing the cap 17, the plastic between cap 17 and body 16 is thin and presents a plane of weakness, making it easy to tear off the cap. The body 16 of unit-dose vial 15 is then inserted into the lower body 80, as shown by the dotted lines of FIG. 1, so that a dip tube 93 will be adjacent the bottom of the body 16. The lower body 80 has cut-outs 81 which permit the sides of the body 16 of the unit-dose vial 15 to be grasped while the body 16 is being inserted into position. After the body 16 of unit-dose vial 15 is seated, a pliable sleeve 14 (FIG. 5) may be slipped over the main body 80 and the part of the lower body 80 below the inlet tube 61. This sleeve protects the body 16 of the unit-dose vial 15 from being disturbed by jostling, so that the body 16 remains in placing during use. Prior to use and set up of the device of the present invention, the sleeve is previously affixed to protect the lower extremity of the device.

FIG. 3 illustrates the manner of use of the nebulizer. It is held in the hand, much in the manner in which a smoker holds a pipe, and the mouthpiece 12 is placed in the lips. The patient breathes in through the mouthpiece 12 to receive the mist.

The elbow 11 has an opening 19 which is normally uncovered, so that as the patient inhales, air is drawn in through opening 19. A typical flow of gas into the inlet tube 61 is 6 to 8 liters per minute. This is less than a person normally breathes. Therefore, if the patient inhales only through the mouthpiece 12, additional air is breathed in through the opening 19. If the opening 19 is partially or completely blocked, as shown in FIG. 3 by the dotted finger, then less external air can be mixed inside the nebulizer, the concentration of the mist received by the patient is higher. Thus, whenever the patient feels the need for a higher concentration of mist, the need is filled by abstructing the opening 19 by a slight movement of the finger.

Figure 6A:
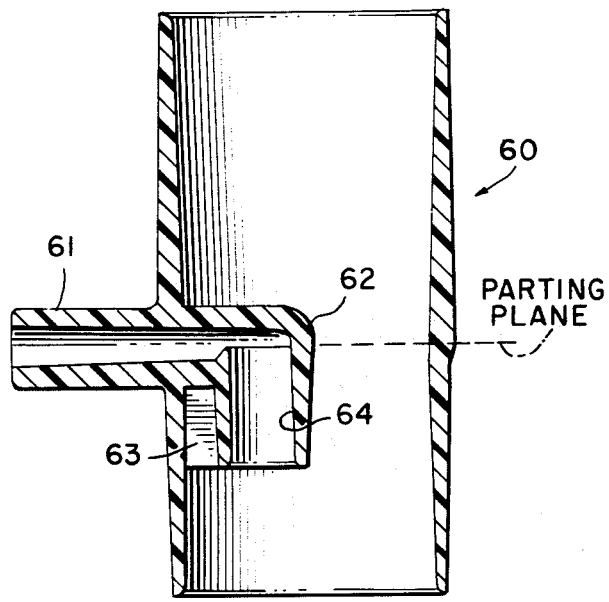
FIGS. 6A, 6B, 6C and 6D are respectively side and front cross-sections taken along the planes 6A—6A and 6B—6B of FIG. 6C, a top view and a bottom view of the upper body of the nebulizer.
Figure 6B:
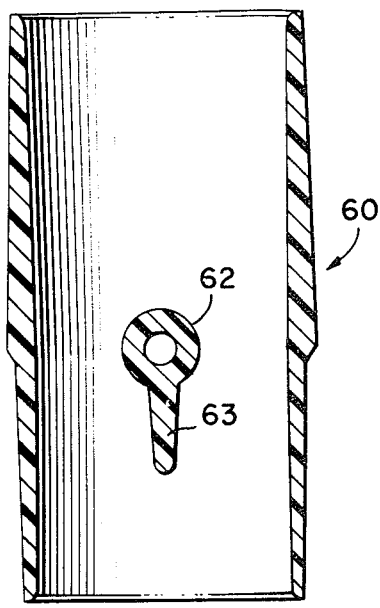
Figure 6C:
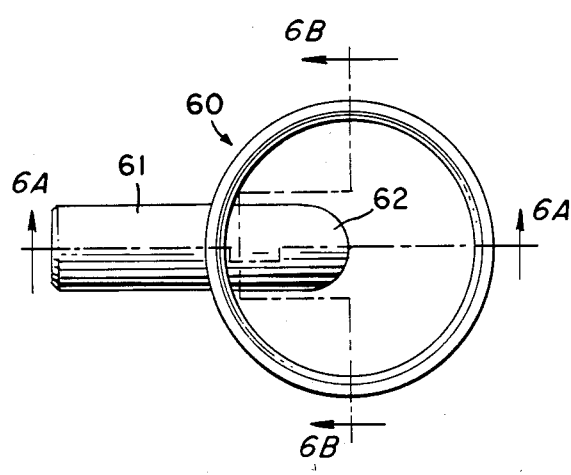
Figure 6D:
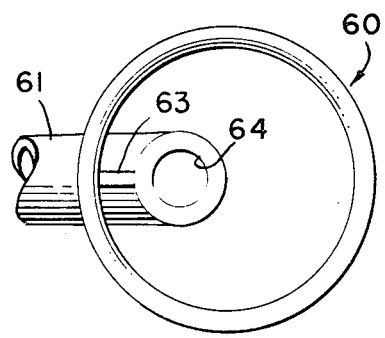

The construction of the upper body 60 of the nebulizer 10 is shown in greater detail in FIGS. 6A to 6D. The upper body is injection molded of ABS or another suitable thermoplastic material. A two part mold, having a side entry core, is used to mold the upper body. The parting plane between the two parts of the mold is depicted in FIG. 6A. It will be seen in FIG. 6A that the surfaces of the upper body are provided with a draft (i.e., a taper) to permit the upper mold to be withdrawn upwardly from the parting plane and to permit the lower mold to be similarly withdrawn downwardly. Furthermore, the interior of inlet tube 61 is provided with a draft to permit the core which forms the interior to be withdrawn towards the left. No similar draft is needed for the outside of inlet tube 61 because the outside is molded by the upper and lower molds, which do not withdraw sidwardly. The elbow 62 is provided with a strengthening web 63.

The venturi 70 which forms the mist is shown in detail in FIGS. 7A to 7D. This part is injection molded to precision standards from nylon or some other thermoplastic material which will hold close tolerances. The part is molded in a two-piece die having separate cores for the bores 71, 72 and 73 (FIG. 7B). The parting plane for the two parts of the die is shown in FIG. 7A.

As can be seen from FIGS. 7A to 7B, the bores 71 and 73 have a draft to permit withdrawal of the cores by which they are molded. The bore 72 also has a suitable taper, too small to be depicted in the drawing. The outer surface 74 of the portion forming bore 71 need not be similarly tapered since the molds which form the outer surface 74 do not withdraw upwardly. The outer surface 77 of the portion forming the bore 73 is tapered, not because of a mold-release problem, but to save material.

The exterior surface 74 fits the bore 64 of the upper body when venturi 70 is united with the upper body 60. Thus, bore 71 receives the flow of gas which comes from inlet tube 61, by way of flow through elbow 62. The rib 75, as is known in the art, serves to help establish a leak-proof connection between elbow 62 and bore 71.

Figure 9:
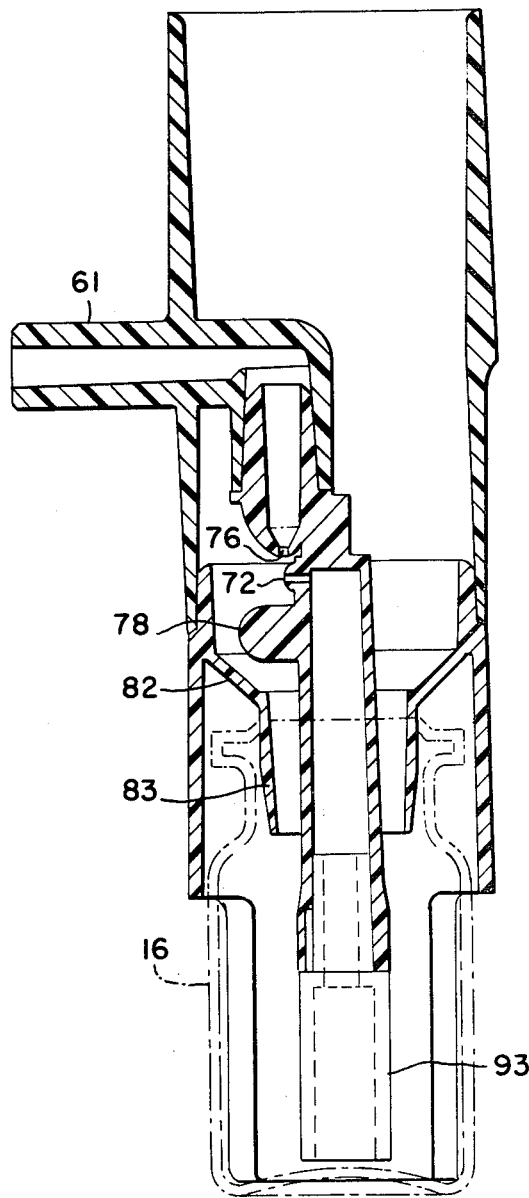
FIG. 9 is a side view, in cross-section, showing in detail how the parts of FIGS. 6 to 8 fit together and how a unit-dose vial is combined therewith.

The lower end of the venturi 70 is adapted to be extended with a dip tube 93, as can be seen in FIG. 9. The dip tube 93 is made of ABS or another suitable thermoplastic material, rather than of nylon, in order to reduce the size and cost of the expensive precision molding seen in FIG. 7B. The dip tube 93 is cemented to the bore 73 by first depositing a small amount of cement in recess 79, inserting the upper end of dip tube 93 in the bore 73, and then rotating the dip tube with respect to the bore 73 to distribute the cement about the outer periphery of the portion of dip tube 93 adjacent recess 79.

In operation, the flow of gas into inlet tube 61 through elbow 62 is directed to nozzle 76 and forms a gas jet past the bore 72. As is understood in the art, the rapid flow of gas past the outer end of bore 72 reduces the air pressure thereat because of the Bernoulli effect. If the lower end of the dip tube 93 is immersed in fluid contained in the body 16 of a unit-dose vial 15, some of the fluid will be sucked up into bore 73 and on up to bore 72 and out into the gas jet. The miniscus of liquid, which forms at the outer end of bore 72 is disturbed and torn by the gas jet from nozzle 76, thereby entraining globules of moisture of various sizes in the gas jet. The gas jet hits a knob 78 and is deflected. During this deflection, the smaller globules of moisture are carried along with the deflected gas jet, while the larger ones are not carried along with the deflected gas jet but instead impinge on knob 78. The knob 78, therefore, acts as a separator for trapping the larger globules while permitting the smaller globules to be carried along as a mist. The differing sizes of globules are affected differently because as the size of a globule varies, the sail-area varies as the square of the diameter while the inertia-mass varies as the cube of the diameter.

While a venturi such as disclosed will operate over a wide variation of design, the relationship depicted in FIG. 7D optimizes operation. It will be noted that the bore 72 protrudes into the gas jet an amount slightly past the center line of the jet. Furthermore, the flat plane surrounding the outer end of bore 72 is tilted slightly so as to be relieved at the downstream side, with respect to the gas jet. For a gas flow of 6 to 8 liters per minute, the following parameters provide very satisfactory operation:

| | |
|---|---|
| Diameter of bore 76 | 0.025" |
| Diameter of bore 72 | 0.036" |
| Diameter of tilted flat plane | 0.050" |
| Radius of spherical outer surface of water nozzle | 0.062" |
| Distance, bottom of 76 to center line of 72 | 0.056" |
| Linear offset | 0.004" |
| Angular clearance | 1.5° |

Figure 8A:
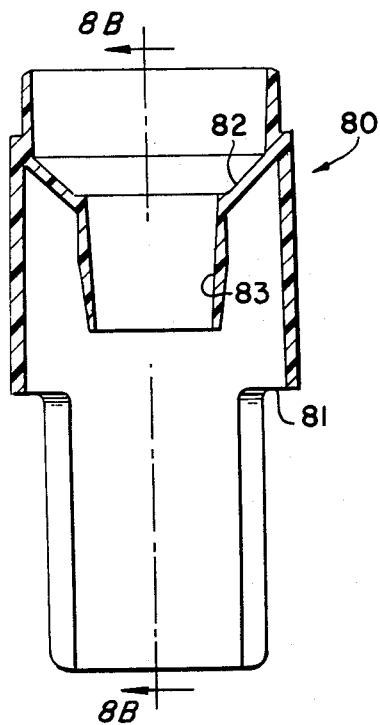
Figure 8C:
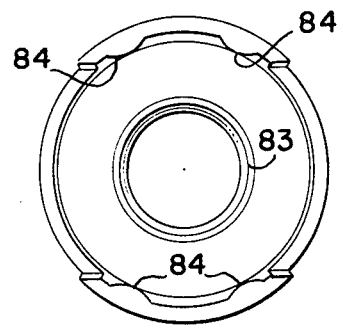
FIG. 8C is a bottom view of the lower body of the nebulizer.
Figure 8B:
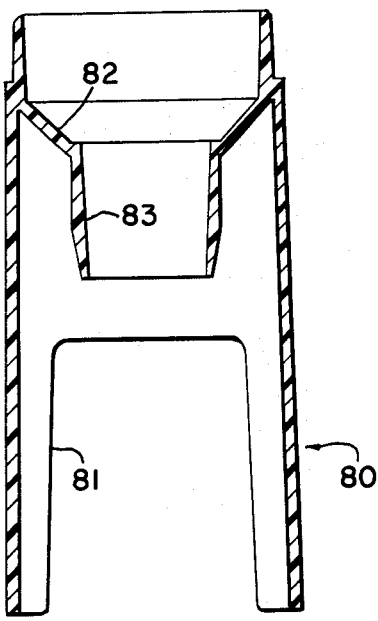

The lower body and vial holder 80 is shown in detail in FIGS. 8A to 8C. The upper end of the lower body 80 is adapted to be united with the lower end of the upper body, as can be seen in FIG. 9. Lower body includes a funnel 82 and a coupling 83. The funnel 82 collects the drip of larger globules of moisture from the upper body 60 (principally from the knob 78) and delivers this moisture to coupling 83, which feeds it to the body 16 of the unit-dose vial.

Thus, excess moisture which is not delivered to the mouth-piece 12 recycled back to the vial. Furthermore, the outer side of coupling 83 is tapered, to snugly fit the opening in the body 16 of the unit-dose vial.

Thus, excess moisture which is not delivered to the mouth-piece 12 is recycled back to the vial. Furthermore, the outer side of coupling 83 is tapered, to snugly fit the opening in the body 16 of the unit-dose vial. The snug fit prevents leakage of moisture from the body 16 of the unit-dose vial, in the event the patient shakes the nebulizer 10. The ribs 84 seen in FIG. 8C help to frictionally retain the body 16 of the unit-dose vial in operative position with the dip tube 93 and funnel 83. As previously mentioned in connection with FIG. 5, a pliable sleeve 14 is used to protect the vail from unintended disengagement from the nebulizer 10.

What is claimed is:

1. A nebulizer connector comprising means adapted to removably hold an open-top receptacle in relationship with a suction tube, which extends in an up and down direction, so that said suction tube has a lower end positioned within and adjacent the bottom of said receptacle;

whereby an open-top receptacle of liquid can be readily held, emptied by said suction tube, removed and replaced by another open-top receptacle of liquid;

said means comprising a hollow cylinder extending in an up and down direction about said suction tube, having a lower end roughly coextensive with said lower end of said suction tube and having inner dimensions closely fitting the outer dimensions of said open-top receptacle, said hollow cylinder having a means for supporting said suction tube in a coaxial relationship with said hollow cylinder;

said hollow cylinder having, adjacent its lower end, cutouts extending to the lower end of said hollow cylinder, permitting the sides of said receptacle to be grasped by the fingers when the receptacle is held in said means.

2. A nebulizer connector comprising means adapted to removably hold the nebulizer of claim 1 having friction means on the inner face of said hollow cylinder to grasp said open-top receptacle.

3. A nebulizer connector comprising means adapted to removably hold the nebulizer of claim 2 in which said friction means comprises a longitudinal rib on the inner face of said hollow cylinder.

4. A nebulizer for use in treatment of patients and adapted to be held in the patient's hand during use comprising:

a hollow casing having a longitudinal axis which extends in a generally up and down direction when said nebulizer is held in the patient's hand during use, said casing having an upper end and a lower end at opposite ends of said longitudinal axis;

conduit means, adapted to be connected to a source of gas under pressure, extending from the outside of the inside of said casing;

nozzle means, located inside said hollow casing and connected to said conduit means, for producing a gas jet;

a suction tube extending from adjacent the bottom end portion of said casing to adjacent said nozzle means and protruding thereat into said gas jet so that said gas jet is in aspirating relationship with said suction tube;

an opening in said lower end, adapted to removably receive an open-top receptacle of liquid so that the said suction tube extends through said open top to near the bottom end of said receptacle, whereby said gas jet will aspirate said liquid from said receptacle and nebulize it;

the nebulized liquid in said gas jet comprising a mist having liquid globules of varying sizes, the smaller of which remain suspended in the gas and the larger of which settle out;

funnel means located within said casing between said nozzle and said receptacle to intercept and collect moisture which descends to said funnel from above;

said funnel means having a large collection edge joined in liquid-tight manner to the interior of said hollow casing and a small delivery edge, said small delivery edge being located closer to said lower end than said large collection edge, and having a continuous slanting surface between said large collection edge and said small delivery edge;

said small delivery edge being joined in liquid-tight manner to the end of a tubular coupling, the other end of which extends towards said lower end;

the outer side of said coupling being tapered to somewhat decrease in diameter at the end thereof distal from said funnel means;

the taper and size of said tubular coupling being so related to the size of the open-top of the receptacle and the location of said coupling being such, with respect to said opening in said lower end of said casing that, when an open-top receptacle is inserted in said opening, the open-top of said receptacle is wedged in liquid-splash-tight relationship on said tubular coupling into said receptacle;

whereby excess moisture which settles out of said mist is collected by said funnel means and fed through said tubular coupling to said receptacle for recycling up said suction tube.

5. The nebulizer of claim 4 which said nozzle means is supported by said conduit means.

6. The nebulizer of claim 4 in which said nozzle means is disposed so as to produce a generally downwardly directed jet of gas during use of the nebulizer.

7. The nebulizer of claim 4 in which said continuous slanting surface is a truncated cone.

8. The nebulizer of claim 4 having friction means on the inside of said casing to removably retain said receptacle in said nebulizer.

9. The nebulizer of claim 4 in which said casing is a cylinder.

10. The nebulizer of claim 4 having separator means, disposed in the path of said jet of gas, to cause the larger globules of moisture of separate from the mist at the site of said separator means.

11. The nebulizer of claim 4 in which said casing comprises:

an upper body, integrally comprising a cylindrical shell having open ends with said conduit means leading integrally from exterior to interior of said upper body through said shell, said conduit means having at the end thereof within said casing an integral elbow with an open end facing and open end of said upper body; and a lower body integrally comprising a second cylindrical shell, having open first and second ends, the first of which ends is jointed in liquid-tight relationship to an open end of said upper body, a truncated conical funnel integrally joined at its basal outer edge to said second cylindrical shell near the first open end thereof and said truncated conical funnel having its apical inner edge situated closer to said second end thereof than said basal outer edge is situated, a tubular coupling integrally joined at one end to the said apical inner edge and extended at its other end towards said second open end of said lower body; and a nozzle secured to the open end of said elbow, a suction tube integrally joined to said nozzle and having one end adjacent said nozzle, and extending from there through said conical funnel and through said tubular coupling.

12. The nebulizer of claim 11 in which said nozzle means is disposed so as to produce a generally downwardly directed jet of gas during use of the nebulizer.

13. The nebulizer of claim 11 having friction means on the outside of said casing to removably retain said receptacle in said nebulizer.

14. The nebulizer of claim 11 having separator means, disposed in the path of said jet of gas, to cause the larger globules of moisture to separate from the mist at the site of said separator means.

* * * * *